US006281176B1

(12) United States Patent
Cochran et al.

(10) Patent No.: US 6,281,176 B1
(45) Date of Patent: Aug. 28, 2001

(54) PROCESS FOR PRODUCING BETAINE/ AMINE OXIDE MIXTURES

(75) Inventors: Rebecca S. Cochran; Patrick C. Hu; Michael S. McCaig; Edmund F. Perkins, Jr.; Joe D. Sauer; Dustin H. Thomas, all of Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

(21) Appl. No.: 09/454,983

(22) Filed: Dec. 3, 1999

(51) Int. Cl.$^7$ .................. A61K 7/075; C07C 229/10
(52) U.S. Cl. .................. 510/123; 510/124; 510/490; 510/491; 562/575; 564/298
(58) Field of Search .................. 562/575; 564/298; 510/123, 124, 490, 491

(56) References Cited

U.S. PATENT DOCUMENTS

| 3,819,539 | 6/1974 | Bloch et al. | 252/547 |
| 4,247,480 | * 1/1981 | Murata et al. | 564/298 |
| 4,347,381 | 8/1982 | Tuwell | 564/2 |
| 4,416,808 | 11/1983 | Blaschke et al. | 252/547 |
| 4,588,522 | 5/1986 | Blaschke et al. | 252/547 |
| 5,075,498 | 12/1991 | Perine et al. | 562/575 |
| 5,681,972 | 10/1997 | Hamann et al. | 554/69 |
| 5,710,332 | 1/1998 | Phillips et al. | 564/297 |
| 5,877,143 | 3/1999 | Abbas et al. | 510/433 |

FOREIGN PATENT DOCUMENTS

| 258792 | 4/1989 | (CS) . |
| 2063423 | 9/1972 | (DE) . |
| 0756023 | 1/1997 | (EP) . |

OTHER PUBLICATIONS

Chemical Abstract, 1976 # 84:76146g, U.S. Patent 3,920, 731, p. 120.
Nandakumar et al., "Properties and Performance of Alkyl Betaines and Sultaines", J. Oil Technol. Assoc. India, 1979, vol. 11(2), p. 31–34.
Chemical Abstract, 1987 #106:219366q, Spanish Patent 544,844, p. 359.
Chemical Abstract, 1992, # 117:72080h, 1992, Sismondi et al., "New Agents for Vesicular Systems. Part 1. Synthesis of Saturated Perfluoroalkylated Bitailed Amphiphiles", Tenside, Surfactants, Deterg., 1992, vol. 117, p. 125.
Abstract JP 63012333, 1988, 1 page.

* cited by examiner

Primary Examiner—Howard C. Lee
Assistant Examiner—Leigh C. Maier
(74) Attorney, Agent, or Firm—E. E. Spielman, Jr.

(57) ABSTRACT

This invention provides a process for producing a betaine/ amine oxide mixture. This process comprises reacting, in a liquid medium, an alkali metal ω-halocarboxylate with a first tertiary amine of the formula $R^a{}_2R^bN$, wherein each $R^a$ group is a hydrocarbyl group which independently has from 1 to about 4 carbon atoms, and wherein the $R^b$ group is a hydrocarbyl group which has from about 8 to about 24 carbon atoms, to produce a betaine product solution. To the betaine product solution is added a second tertiary amine of the formula $R^a{}_2R^bN$, wherein each $R^a$ group is a hydrocarbyl group which independently has from 1 to about 4 carbon atoms, and wherein the $R^b$ group is a hydrocarbyl group which has from about 8 to about 24 carbon atoms, to produce an amine/betaine mixture. The first and second tertiary amines can be separate portions of the same amine. Preferably, however, the first and second tertiary amines differ from each other. In a carbon dioxide atmosphere, the amine/betaine mixture is mixed with hydrogen peroxide to yield a betaine/amine oxide mixture.

30 Claims, No Drawings

PROCESS FOR PRODUCING BETAINE/AMINE OXIDE MIXTURES

TECHNICAL FIELD

This invention relates to processes for preparing betaine/amine oxide mixtures from tertiary amines.

BACKGROUND

Many methods exist for making betaine/amine oxide mixtures. Very pure betaine/amine oxide mixtures are needed, particularly for pharmaceutical applications. Thus, there is a need for an efficient process for forming these betaine/amine oxide mixtures in high purity. It would be particularly advantageous if such a process did not require a separate purification step.

THE INVENTION

This invention provides a one-pot process for producing high purity betaine/amine oxide mixtures. A first reaction produces a betaine, and a second reaction produces an amine oxide, resulting in a betaine/amine oxide mixture. The high purity is achieved via separate additions of tertiary amine, which results in greater consumption of ω-halocarboxylate, and oxidation of virtually all free amine that has not been converted to betaine.

Accordingly, an embodiment of this invention provides a process for producing a betaine/amine oxide mixture. This process comprises reacting, in a liquid medium, an alkali metal ω-halocarboxylate with a first tertiary amine of the formula $R^a_2 R^b N$, wherein each $R^a$ group is a hydrocarbyl group which independently has from 1 to about 4 carbon atoms, and wherein the $R^b$ group is a hydrocarbyl group which has from about 8 to about 24 carbon atoms, to produce a betaine product solution. To the betaine product solution is added a second tertiary amine of the formula $R^a_2 R^b N$, wherein each $R^a$ group is a hydrocarbyl group which independently has from 1 to about 4 carbon atoms, and wherein the $R^b$ group is a hydrocarbyl group which has from about 8 to about 24 carbon atoms, to produce an amine/betaine mixture. In a carbon dioxide atmosphere, the amine/betaine mixture is mixed with hydrogen peroxide to yield a betaine/amine oxide mixture. The first and second tertiary amines can be separate portions of the same amine. Preferably, however, the first and second tertiary amines differ from each other.

This invention provides several advantages. The process of the invention can be conducted in one pot. No further steps beyond the one-pot process described herein are necessary to produce a very pure betaine/amine oxide mixture. The produced betaine/amine oxide mixture has a low free amine content (usually about 0.5 wt % or less), a very low nitrosodimethylamine content (usually about 5 parts per billion or less), and a low alkali metal ω-halocarboxylate content (usually about 0.05 wt % or less).

Further embodiments and features of the invention will be apparent from the ensuing description and appended claims.

A variety of solvents, or mixtures thereof, may be used as the liquid medium in this invention. Types of solvents include water, alcohols, esters, and ethers. Examples of suitable alcohols include methanol, ethanol, ethylene glycol, n-propanol, 2-propanol, 2-methyl-1-propanol, propylene glycol, n-butanol, 3-pentanol, cyclopentanol, 2-hexanol, 2-heptanol, and 1-octanol. Suitable esters include methyl acetate, ethyl acetate, methyl propionate, and ethyl propionate. Ethers suitable for use as the liquid medium include diethyl ether, ethyl n-propyl ether, diisopropyl ether, tetrahydrofuran, methyltetrahydrofuran, 1,4-dioxane, 1,3-dioxolane, cyclohexylmethyl ether, glyme (the dimethyl ether of ethylene glycol), diglyme (the dimethyl ether of diethylene glycol), triglyme, and tetraglyme. Preferred solvents are water and ethanol. Highly preferred as the liquid medium is water.

The alkali metal ω-halocarboxylate is preferably the lithium, sodium, or potassium ω-halocarboxylate, and may be produced by the combination of alkali metal hydroxide with the appropriate ω-halocarboxylic acid. More preferably, the alkali metal ω-halocarboxylate is the sodium or potassium ω-halocarboxylate, and most preferably is the sodium ω-halocarboxylate. The ω-halocarboxylate may be, for example, haloacetate, 3-halopropionate, 4-halobutyrate, or 5-halovalerate. Most preferred as the ω-halocarboxylate is haloacetate. The halogen atom of the ω-halocarboxylate may be a chlorine, bromine, or iodine atom, is preferably a chlorine or bromine atom, and most preferably is a chlorine atom. Thus, the most preferred alkali metal ω-halocarboxylates are sodium chloroacetate and sodium bromoacetate; sodium chloroacetate is most highly preferred.

Both the first tertiary amine and the second tertiary amine used in the process of this invention have the formula $R^a_2 R^b N$. $R^a$ is a hydrocarbyl group which has from 1 to about 4 carbon atoms. Suitable hydrocarbyl groups include methyl, ethyl, isopropyl, cyclopropyl, sec-butyl, tert-butyl, n-butyl, and cyclobutyl. While $R^a$ is preferably a straight chain, it may also be a branched or cyclic hydrocarbyl group. The two $R^a$ groups may be the same or different, but are preferably the same. It is highly preferred that both $R^a$ groups are methyl groups. $R^b$ is a hydrocarbyl group which has from about 8 to about 24 carbon atoms. Examples of suitable hydrocarbyl groups include, but are not limited to, octyl, 4-methylcyclooctyl, nonyl, 3-nonenyl, decyl, 3-methyl-5-undecenyl, dodecyl, tetradecyl, 8-cyclohexyloctyl, 6-ethyldodecyl, hexadecyl, octadecyl, eicosyl, and n-tetracosyl. $R^b$ may be a straight chain, a branched, or a cyclic group, but is preferably a straight chain hydrocarbyl group. Saturated hydrocarbyl groups are preferred, although $R^b$ may be an unsaturated hydrocarbyl group. Preferably, $R^b$ has from about 8 to about 18 carbon atoms. Highly preferred as the hydrocarbyl group of $R^b$ are a n-tetradecyl group and a n-hexadecyl group. The most highly preferred tertiary amines are thus N,N-dimethyltetradecylamine and N,N-dimethylhexadecylamine. Particularly preferred is the use of N,N-dimethylhexadecylamine as the first tertiary amine and N,N-dimethyltetradecylamine as the second tertiary amine.

As noted above, the betaine and the amine oxide may be synthesized from different amines or from two separate additions of the same amine. While less preferred, the first amine and/or the second amine may comprise a mixture of two or more amines. An advantage of adding the amine(s) in two separate steps is that the proportion of amine that forms betaine and the proportion of amine that forms amine oxide can be controlled. Selection of which amine forms the betaine and which forms the amine oxide is another advantage of separate addition of the amines when the first amine and the second amine are different.

When reacting an alkali metal ω-halocarboxylate with a first tertiary amine, a slight excess of the alkali metal ω-halocarboxylate relative to the tertiary amine is preferred. The liquid medium may be added to the reaction vessel prior to both the amine and the alkali metal ω-halocarboxylate, or concurrently with them. One or both reactants may be co-fed to the reaction vessel with the liquid medium. A preferred addition method is mixing the amine with liquid medium, followed by the addition of alkali metal ω-halocarboxylate dissolved in another portion of liquid medium. More preferably, the alkali metal ω-halocarboxylate in a portion of liquid medium is added to a solution of amine in liquid medium which has already been heated to the desired reaction temperature. For this reaction, the temperature may be in the range of from about 60° C. to about 100° C., and preferably is in the range of from about 70° C. to about 90° C. The pH of the solution should be in the range of from about 7.5 to about 12, and is preferably in the range of from about 8 to about 10. Often, the addition of base during the reaction is necessary to maintain the pH in the desired range. Such base may be added periodically or continuously. Preferred bases are the alkali metal hydroxides, and sodium hydroxide is the most preferred base. Reaction times typically range from about 3 hours to about 48 hours. More preferable reaction times are in the range of from about 10 hours to about 30 hours. A betaine product solution is obtained; it is made up predominately of betaine and liquid medium, but small amounts of unreacted amine and alkali metal ω-halocarboxylate are usually also present.

A second tertiary amine is added to the betaine product solution. When the second tertiary amine has fewer carbon atoms in the $R^b$ group than the first tertiary amine does, the presence of the second amine lowers the viscosity of the mixture. Remaining ω-halocarboxylate is consumed when the second tertiary amine is added. To maximize the consumption of the remaining ω-halocarboxylate, it is preferred to stir the amine/betaine mixture for a time in the range of from a few minutes to about four hours, and more preferably for about one hour to about three hours.

While it is known in the art that amine oxides can be made without carbon dioxide, its presence is advantageous. The carbon dioxide acts as a catalyst, speeding the reaction between the amine and the hydrogen peroxide.

Carbon dioxide is typically added to the vapor space above the amine/betaine reaction mixture. Because the advantages provided by carbon dioxide are maximized by having it present from the beginning of the reaction, it is preferable to add the carbon dioxide to the amine/betaine mixture prior to adding the hydrogen peroxide. A slight stoichiometric excess of hydrogen peroxide relative to the second tertiary amine is preferred. Generally, an aqueous solution of hydrogen peroxide is used. The hydrogen peroxide may be added all at once, or preferably, slowly over time. More preferably, the amine/betaine mixture is heated to the desired reaction temperature before adding the hydrogen peroxide. The temperature for the reaction may be in the range of from about 35° C. to about 85° C., and preferably is in the range of from about 50° C. to about 80° C. Reaction times are in the range of from about 2 hours to about 24 hours, and preferably are in the range of from about 3 hours to about 20 hours. Normally, a betaine/amine oxide mixture of high purity is produced.

The following examples are presented for purposes of illustration, and are not intended to impose limitations on the scope of this invention.

EXAMPLE 1

416.7 g of N,N-dimethylhexadecylamine (1.546 mol) and 1003 g water are added to a 5 liter round bottom flask; the solution is heated to 80° C. Sodium chloroacetate is dissolved in 816 g water and this solution is then added to the reaction flask. For 24 hours, the reaction flask is maintained at 80° C. while the pH is maintained between 8–9 using 25% NaOH (36 g). The betaine product contained 18.6 wt % cetyl betaine (1.4 mol) and 1.55 wt % free amine.

338.1 g of N,N-dimethyltetradecylamine (1.40 mol) and 480 g water are added to the betaine product mixture. Carbon dioxide is added to the head space of the reaction flask. 180.2 g of 35% hydrogen peroxide (1.86 mol) is then added, while maintaining the solution at 60–70° C.; some foaming occurs. The solution is maintained at 60–70° C. for approximately 4 hours. The product contains 13.3 wt % betaine (as dimethylhexadecylamine betaine), 11.1 wt % amine oxide (as dimethyltetradecylamine oxide), and 0.41 wt % free amine.

EXAMPLE 2

The procedure of Example 1 was repeated, varying only the amounts of reagent used. The amine/water solution is made from 427.1 g of N,N-dimethylhexadecylamine and 1010.7 g of water; the sodium chloroacetate solution contains 212.3 g of sodium chloroacetate and 921 g of water. The pH is maintained by the addition of 15.45 g of 25% NaOH. At the end of this reaction, the solution contains 19.1 wt % dimethylhexadecylamine betaine, and 0.92 wt % free amine.

730 g of water and 361.5 g of N,N-dimethyltetradecylamine are added to the reaction mixture, and carbon dioxide is added to the vapor space of the reaction flask. 184.8 g of 35% $H_2O_2$ is then added. The resultant product mixture contains 14.1 wt % dimethylhexadecylamine betaine, 11.4 wt % dimethyltetradecylamine oxide, and 0.37 wt % free amine.

EXAMPLE 3

447.2 g of N,N-dimethylhexadecylamine (1.659 mol) and 1004 g water are added to a 5 liter round bottom flask; the solution is heated to 82° C. 222.2 g of sodium chloroacetate (1.92 mol) is dissolved in 914 g water and this solution is then added to the reaction flask. For 23 hours, the reaction flask is maintained at 80° C. while a basic pH is maintained using 25% NaOH. 301 g of water is added to this betaine product solution to increase its fluidity.

362.5 g of N,N-dimethyltetradecylamine (1.50 mol) and 700 g of water are added to the betaine product mixture. The temperature of the amine/betaine mixture is decreased to 65° C. Carbon dioxide is added to the head space of the reaction flask. 193.4 g of 35% hydrogen peroxide (1.99 mol) is then added during 90 minutes while maintaining the solution at 60–70° C. The solution is maintained at 60° C. for another 18 hours. The product contains 12.9 wt % betaine (as dimethylhexadecylamine betaine), 10.0 wt % amine oxide (as dimethyltetradecylamine oxide), and 0.47 wt % free amine, as determined by NMR. The nitrosodimethylamine content, determined by gas chromatography, was 3 parts per billion.

A portion of the obtained product was diluted with water to reduce the concentration of the active ingredients (betaine+amine oxide) to 10 wt %, and the pH was adjusted to 4.8. This 10 wt % product solution contains less than 5 parts per billion of nitrosodimethylamine.

EXAMPLE 4

N,N-dimethylhexadecylamine and water are added to a reaction flask; the solution is heated. Sodium chloroacetate is dissolved in water and this solution is then added to the reaction flask. The reaction flask is maintained at 80° C.

while a basic pH is maintained using aqueous NaOH. At the end of this reaction, the solution contains 21 wt % dimethylhexadecylamine betaine, 0.94 wt % free amine, and 0.21 wt % sodium chloroacetate.

N,N-dimethyltetradecylamine is added to the betaine product mixture, and the solution is heated for one hour. The resultant mixture contains 17.9 wt % dimethylhexadecylamine betaine and 14.8 wt % free amine. 0.04 wt % sodium chloroacetate is present, a 78% reduction from the amount at the end of the dimethylhexadecylamine betaine reaction.

EXAMPLE 5

150 lb. of N,N-dimethylhexadecylamine ($6.75 \times 10^4$ g, 251 mol) and 300 lb. (135 L) of water are added to a reactor; the solution is heated to 80° C. 68 lb. of sodium chloroacetate ($3.06 \times 10^4$ g, 263 mol) are added to the reactor, along with another 300 lb. (135 L) of water. For 18 hours, the reactor is maintained at 80° C. More sodium chloroacetate is then added, and the solution is kept at 80° C. for another 4 hours.

120 lb. of N,N-dimethyltetradecylamine ($5.4 \times 10^4$ g, 224 mol) are added to the reactor, and the solution therein is stirred for two hours to reduce the amount of sodium chloroacetate. Carbon dioxide is added to the head space of the reactor. 60 lb. of 35% hydrogen peroxide ($2.7 \times 10^4$ g, 278 mol) and 220 lb. (99 L) of water are then added, while maintaining the solution at 60–70° C. The solution is maintained at 60–70° C. for 18 hours. Enough water was then added to reduce the concentration of the active ingredients (betaine+amine oxide) to 10 wt %, and the pH was adjusted to 4–6 with citric acid. The 10 wt % product solution contains less than 0.05 wt % free amine, less than 0.02 wt % sodium chloroacetate, as determined by NMR. The nitrosodimethylamine content of the 10 wt % product solution is less than 5 parts per billion.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. Whatever transformations, if any, that occur in situ as a reaction is conducted is what the claim is intended to cover. Thus the fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process which comprises
   a) reacting, in an alkaline liquid medium, an alkali metal ω-halocarboxylate with a first tertiary amine of the formula $R^a_2R^bN$, wherein each $R^a$ group is a hydrocarbyl group which independently has from 1 to about 4 carbon atoms and the $R^b$ group is a hydrocarbyl group which has from about 8 to about 24 carbon atoms, to produce an alkaline betaine product solution;
   b) adding to said alkaline betaine product solution a second tertiary amine of the formula $R^a_2R^bN$, wherein each $R^a$ group is a hydrocarbyl group which independently has from 1 to about 4 carbon atoms and the $R^b$ group is a hydrocarbyl group which has from about 8 to about 24 carbon atoms to produce an amine/betaine mixture, said second tertiary amine being the same as or different from said first tertiary amine; and
   c) mixing, in a carbon dioxide atmosphere, said amine/betaine mixture and hydrogen peroxide to produce a betaine/amine oxide mixture.

2. A process according to claim 1 wherein said second tertiary amine is the same species as said first tertiary amine.

3. A process according to claim 1 wherein said second tertiary amine is a different species from said first tertiary amine.

4. A process according to claim 1 wherein said liquid medium is water.

5. A process according to claim 1 wherein said ω-halocarboxylate is a haloacetate.

6. A process according to claim 1 wherein the alkali metal of said alkali metal ω-halocarboxylate is sodium.

7. A process according to claim 1 wherein at least one $R^a$ group of said first tertiary amine is a methyl group.

8. A process according to claim 1 wherein $R^b$ of said first tertiary amine has from about 8 to about 18 carbon atoms.

9. A process according to claim 1 wherein at least one $R^a$ group of said second tertiary amine is a methyl group.

10. A process according to claim 1 wherein $R^b$ of said second tertiary amine has from about 8 to about 18 carbon atoms.

11. A process according to claim 1 wherein said first tertiary amine is N,N-dimethylhexadecylamine, and wherein said second tertiary amine is N,N-dimethyltetradecylamine.

12. A process according to claim 1 wherein the amount of free amine present in said betaine/amine oxide mixture is no greater than 0.5 wt %.

13. A process according to claim 1 wherein the amount of nitrosodimethylamine present in said betaine/amine oxide mixture is no greater than 5 parts per billion.

14. A process according to claim 1 wherein the amount of alkali metal ω-halocarboxylate present in said betaine/amine oxide mixture is no greater than 0.05 wt %.

15. A process according to claim 1 wherein the temperature in a) is in the range of from about 60° C. to about 100° C.

16. A process according to claim 1 wherein the temperature in c) is in the range of from about 35° C. to about 85° C.

17. A process according to claim 1 wherein the pH in a) is in the range of from about 7.5 to about 12.

18. A process according to claim 1 wherein said liquid medium is water and wherein said alkali metal ω-halocarboxylate is sodium chloroacetate or sodium bromoacetate.

19. A process according to claim 18 wherein said first tertiary amine is N,N-dimethylhexadecylamine, and wherein said second tertiary amine is N,N-dimethyltetradecylamine.

20. A process according to claim 18 wherein the amount of free amine present in said betaine/amine oxide mixture is no greater than 0.5 wt %, and wherein the amount of nitrosodimethylamine present in said betaine/amine oxide mixture is no greater than 5 parts per billion.

21. A process according to claim 18 wherein the temperature in a) is in the range of from about 60° C. to about 100° C., and wherein the temperature in c) is in the range of from about 35° C. to about 85° C.

22. A process according to claim 1 wherein the amount of alkali metal ω-halocarboxylate present in said betaine/amine oxide mixture is no greater than 0.05 wt %.

23. A process according to claim 18 wherein the pH in a) is in the range of from about 7.5 to about 12.

24. A process according to claim 1 wherein said liquid medium is water, wherein said first tertiary amine is N,N-dimethylhexadecylamine, wherein said second tertiary amine is N,N-dimethyltetradecylamine, wherein the temperature in a) is in the range of from about 60° C. to about 100° C., wherein the temperature in c) is in the range of from about 35° C. to about 85° C., wherein the pH in a) is in the range of from about 7.5 to about 12, wherein the amount of free amine present in said betaine/amine oxide mixture is no greater than 0.5 wt %, wherein the amount of nitrosodimethylamine present in said betaine/amine oxide mixture is no greater than 5 parts per billion, and wherein the amount of alkali metal ω-halocarboxylate present in said betaine/amine oxide mixture is no greater than 0.05 wt %.

25. A process according to claim 24 wherein said alkali metal ω-halocarboxylate is sodium chloroacetate.

26. A process which comprisese
  a) adding an aqueous solution of an alkali metal ω-halocarboxylate to an aqueous solution of a first tertiary amine of the formula $R^a_2R^bN$, wherein each $R^a$ group is a hydrocarbyl group which independently has from 1 to about 4 carbon atoms and the $R^b$ group is a hydrocarbyl group which has from about 8 to about 24 carbon atoms, and maintaining the pH of the resultant solution in the range of from about 7.5 to about 12, to produce an alkaline betaine product solution;
  b) adding to said alkaline betaine product solution a second tertiary amine of the formula $R^a_2R^bN$, wherein each $R^a$ group is a hydrocarbyl group which independently has from 1 to about 4 carbon atoms and the $R^b$ group is a hydrocarbyl group which has from about 8 to about 24 carbon atoms to produce an amine/betaine mixture, said second tertiary amine being the same as or different from said first tertiary amine; and
  c) mixing, in a carbon dioxide atmosphere, said amine/betaine mixture and aqueous hydrogen peroxide to produce a betaine/amine oxide mixture.

27. A process according to claim 26 wherein both $R^a$ groups of said first tertiary amine are methyl groups; wherein $R^b$ of said first tertiary amine has from about 8 to about 18 carbon atoms; wherein both $R^a$ groups of said second tertiary amine are methyl groups; wherein $R^b$ of said second tertiary amine has from about 8 to about 18 carbon atoms; wherein the alkali metal of said alkali metal ω-halocarboxylate is sodium; wherein the pH of said resultant solution is maintained in the range of from about 8 to about 10 by addition of base, periodically or continuously, to the mixture in a); wherein the temperature in a) is in the range of from about 60° C. to about 100° C.; wherein the temperature inc) is in the range of from about 35° C. to about 85° C.; wherein the amount of nitrosodimethylamine present in said betaine/amine oxide mixture is no greater than 5 parts per billion; and wherein the amount of alkali metal ω-halocarboxylate present in said betaine/amine oxide mixture is no greater than 0.05 wt %.

28. A process according to claim 27 wherein in a) the aqueous solution of the sodium ω-halocarboxylate is added to the aqueous solution of the first tertiary amine which has already been heated to a temperature in the range of about 60° C. to about 100° C.; and wherein said second tertiary amine has fewer carbon atoms in the $R^b$ group than said first tertiary amine.

29. A process according to claim 28 wherein said first tertiary amine is N,N-dimethylhexadecylamine; wherein said second tertiary amine is N,N-dimethyltetradecylamine; and wherein said alkali metal ω-halocarboxylate is sodium chloroacetate or sodium bromoacetate.

30. A process according to claim 27 wherein the temperature in a) is in the range of from about 70° C. to about 90° C.; wherein the temperature in c) is in the range of from about 50° C. to about 80° C.; and wherein said second tertiary amine has fewer carbon atoms in the $R^b$ group than said first tertiary amine.

* * * * *